United States Patent [19]
Lamadrid

[11] 4,227,420
[45] Oct. 14, 1980

[54] PRESSURE COUPLING MECHANISM IN A PRESSURE MONITORING ASSEMBLY
[75] Inventor: Rene G. Lamadrid, Bethesda, Md.
[73] Assignee: Baxter Travenol Laboratories, Inc., Deerfield, Ill.
[21] Appl. No.: 47,568
[22] Filed: Jun. 11, 1979
[51] Int. Cl.³ .............................................. G01L 7/08
[52] U.S. Cl. ...................................... 73/756; 73/706; 73/730; 128/675
[58] Field of Search ................: 73/730, 715, 756, 706; 128/672, 675

[56] References Cited
U.S. PATENT DOCUMENTS

| | | | |
|---|---|---|---|
| 3,142,988 | 8/1964 | Love | 73/730 |
| 3,163,529 | 12/1964 | Jewett | 73/730 |
| 3,418,853 | 12/1968 | Curtis | 73/730 |
| 3,563,095 | 2/1971 | Robinson, Jr. | 73/730 |
| 3,863,504 | 2/1975 | Borsanyi | 73/706 |

Primary Examiner—Donald O. Woodiel
Attorney, Agent, or Firm—Henry W. Collins; Thomas R. Vigil; Paul C. Flattery

[57] ABSTRACT

The pressure monitoring assembly monitors changes in pressure of a fluid passing through the assembly. This is accomplished by passing a liquid through a pressure transfer device having first and second chambers therein separated by a flexible diaphragm. The first chamber has air therein and pressure changes are transmitted across the diaphragm from the second chamber through which the liquid flows. The assembly further includes a pressure transducer and a pressure coupling mechanism for coupling the pressure transfer device to the pressure transducer. The pressure coupling mechanism includes a body having a cylindrical chamber and a piston positioned for movement therein with a piston shaft protruding from a coupling end of the body. The shaft is biased outward from the coupling end of the body by a spring. The coupling end has an O ring seal which forms a seal with the pressure transfer device around an orifice in a wall of the second chamber when the pressure coupling mechanism is mounted to the pressure transfer device. The piston shaft has a through-bore to the cylindrical chamber so that air is trapped in an air passageway comprising the first chamber, the through-bore and the cylindrical chamber. As the pressure transfer device is latched to the pressure coupling mechanism, the shaft and piston are pushed against the spring toward the pressure transducer which is mounted to the body at one end of the cylindrical chamber thereby compressing the trapped air in the air passageway.

32 Claims, 6 Drawing Figures

PRESSURE COUPLING MECHANISM IN A PRESSURE MONITORING ASSEMBLY

BACKGROUND OF THE INVENTION

1. Field of the Invention

The present invention relates to a fluid pressure monitoring assembly, and more particularly to a fluid pressure monitoring assembly including a pressure coupling mechanism for coupling a pressure transducer to a pressure transfer device with a biasing pressure established in the coupling mechanism between the pressure transfer device and the pressure transducer.

2. Description of the Prior Art

Heretofore various pressure monitoring assemblies have been proposed wherein pressure is transmitted through air to a pressure transducer. Examples of such assemblies are disclosed in the following U.S. patents:

| U.S. PAT. NO. | PATENTEE |
| --- | --- |
| 2,566,369 | Putman |
| 2,600,324 | Rappaport |
| 3,099,262 | Bigliano |
| 3,190,122 | Edwards |
| 3,364,749 | Sipin |
| 3,496,775 | Sargent |
| 3,537,357 | Packer |
| 3,738,356 | Workman |
| 3,831,588 | Rindner |
| 3,865,100 | Kanai et al. |
| 3,942,382 | Hok |
| 3,946,724 | LaBalme |

In the Workman U.S. Pat. No. 3,738,356 there is disclosed an intravenous pressure monitor which includes a flexible diaphragm secured over and about an opening leading to a needle. A dowel is situated between the diaphragm and a plate having a coil supported on the other side thereof about a magnet. Movement of the diaphragm is transmitted to the coil which moves relative to the magnet and generates an electrical signal which is used as an indication of pressure changes and causes a current to be applied to the coil to drive the membrane back to its original position.

The Rindner U.S. Pat. No. 3,831,588 discloses a pressure sensing device which includes an electrical pressure sensor mounted in a chamber on one side of a flexible membrane for transmitting external pressure to the sensor and a bellows is provided for varying the pressure in the chamber by known amounts thus enabling calibration of the pressure sensor device prior to use after the sensor has been mounted at its position in the chamber.

Also, heretofore it has been proposed in U.S. Application Ser. No. 843,223 for: MONITOR AND FLUID CIRCUIT ASSEMBLY, the disclosure of which is incorporated herein by reference, to monitor the pressure of liquid passing through tubings which are passed in and out of a centrifuge in a centrifugal liquid processing apparatus. When the liquid is blood which is being separated into components thereof, it is desirable that non-invasive pressure measurements be made and that those parts which are in contact with the blood be disposable to avoid cross-contamination. As described in prior application Ser. No. 843,223, a pressure monitoring assembly having a disposable pressure transfer device therein is coupled to a pressure transducer. The pressure transfer device is made of inexpensive disposable material and consists of a capsule divided by a flexible diaphragm into first and second chambers so that the liquid passing through the second chamber is monitored in a non-invasive manner. The first chamber is in communication with the pressure transducer and the air therein is at atmospheric pressure. It has been found that when the liquid pressure in the second chamber is much higher or lower than the air pressure, inaccurate monitoring results because of pressure loss over the diaphragm due to stretching of the diaphragm.

The pressure monitoring assembly and the coupling mechanism therein of the present invention differs from the assemblies referred to above by providing a coupling mechanism therein for establishing a biasing pressure in the pressure coupling mechanism greater than atmospheric pressure. As will be described in greater detail hereinafter, the biasing pressure is produced by compressing air trapped in the pressure coupling mechanism with a piston. By establishing a biasing pressure in the pressure coupling mechanism in the range of the liquid pressure being monitored, inaccuracies due to pressure loss across the diaphragm due to stretching of the diaphragm are minimized.

SUMMARY OF THE INVENTION

According to the invention there is provided pressure coupling means for coupling a first chamber in a fluid pressure transfer device to a pressure transducer, the chamber having one wall thereof defined by a flexible diaphragm against which fluid pressure to be monitored acts, for establishing a fluid tight air passageway communicating the first chamber in the pressure transfer device to the pressure transducer and for establishing, when coupled between the pressure transfer device and the pressure transducer, a biasing force in said air passageway and the first chamber whereby the diaphragm is urged toward the fluid to be monitored so that when such fluid is present at its expected normal pressure, the diaphragm is in a relaxed unstretched state, said pressure coupling means comprising means for trapping a volume of air in said air passageway and the first chamber when said pressure coupling means is coupled to the pressure transfer device and means for compressing the volume of air in said air passageway and the first chamber to establish a biasing pressure in said air passageway and the first chamber.

Further according to the invention there is provided a pressure monitoring assembly comprising a fluid pressure transfer device having a first chamber therein which has one wall thereof defined by a flexible diaphragm against which fluid pressure to be monitored acts, a pressure transducer and pressure coupling means for coupling said first chamber to said pressure transducer, for establishing a fluid tight air passageway communicating said first chamber to said pressure transducer and for establishing, when coupled between said pressure transfer device and said pressure transducer, a biasing force in said air passageway and said first chamber whereby said diaphragm is urged toward the fluid to be monitored so that when such fluid is present at its expected normal pressure said diaphragm is in a relaxed unstretched state, said pressure coupling means comprising means for trapping a volume of air in said air passageway and said first chamber when said pressure coupling means is coupled to said pressure transfer device and means for compressing the volume of air in said air passageway and said first chamber to establish a biasing pressure in said air passageway and said first chamber.

DESCRIPTION OF THE PREFERRED EMBODIMENT

Figures 1, 4:
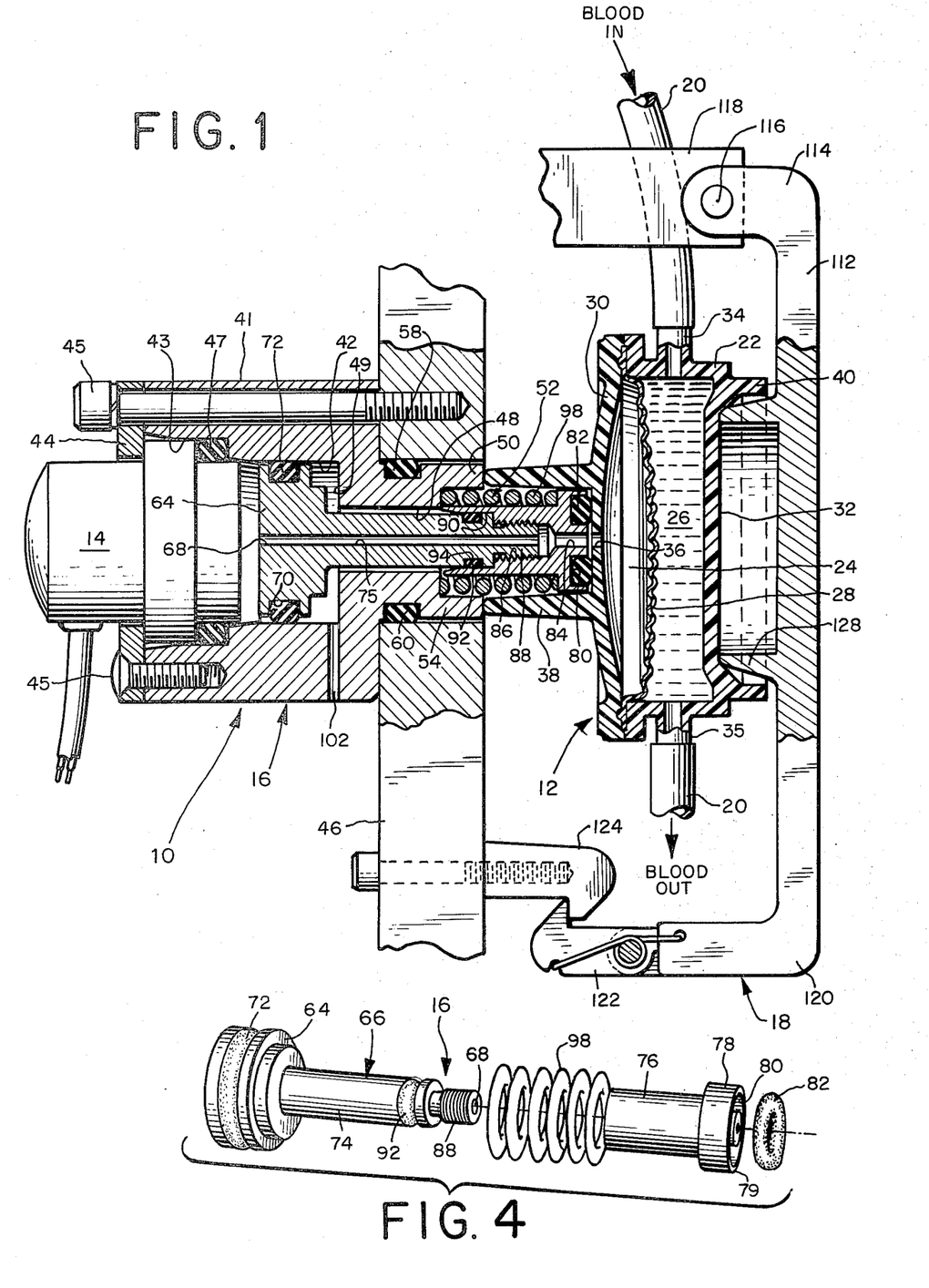
FIG. 1 is a part sectional view of the pressure monitoring assembly of the present invention in its operational position.
FIG. 4 is an exploded perspective view of the piston shaft assembly of the pressure coupling mechanism.

Referring now to the drawings in greater detail there is illustrated in FIG. 1 a pressure monitoring assembly 10 constructed in accordance with the teachings of the present invention. The pressure monitoring assembly 10 includes a pressure transfer device 12 coupled to a commercially available pressure transducer 14 through a pressure coupling mechanism 16. The assembly 10 also includes a latching mechanism 18 for latching the pressure transfer device 12 with the pressure coupling mechanism 14.

The pressure monitoring assembly 10 monitors pressure of a liquid such as blood flowing through a tubing 20 in a machine such as the Centrifugal Liquid Processing Apparatus sold by American Instrument Company, a division of Baxter Travenol Laboratories, Inc. of Deerfield, Illinois, under the trademark "Cell Separator".

Further details of the fluid circuit with which the assembly 10 is used are set forth in application Ser. No. 843,223 for: MONITOR AND FLUID CIRCUIT ASSEMBLY filed on Oct. 18, 1977, the disclosure of which is incorporated herein by reference.

Figures 2, 3:
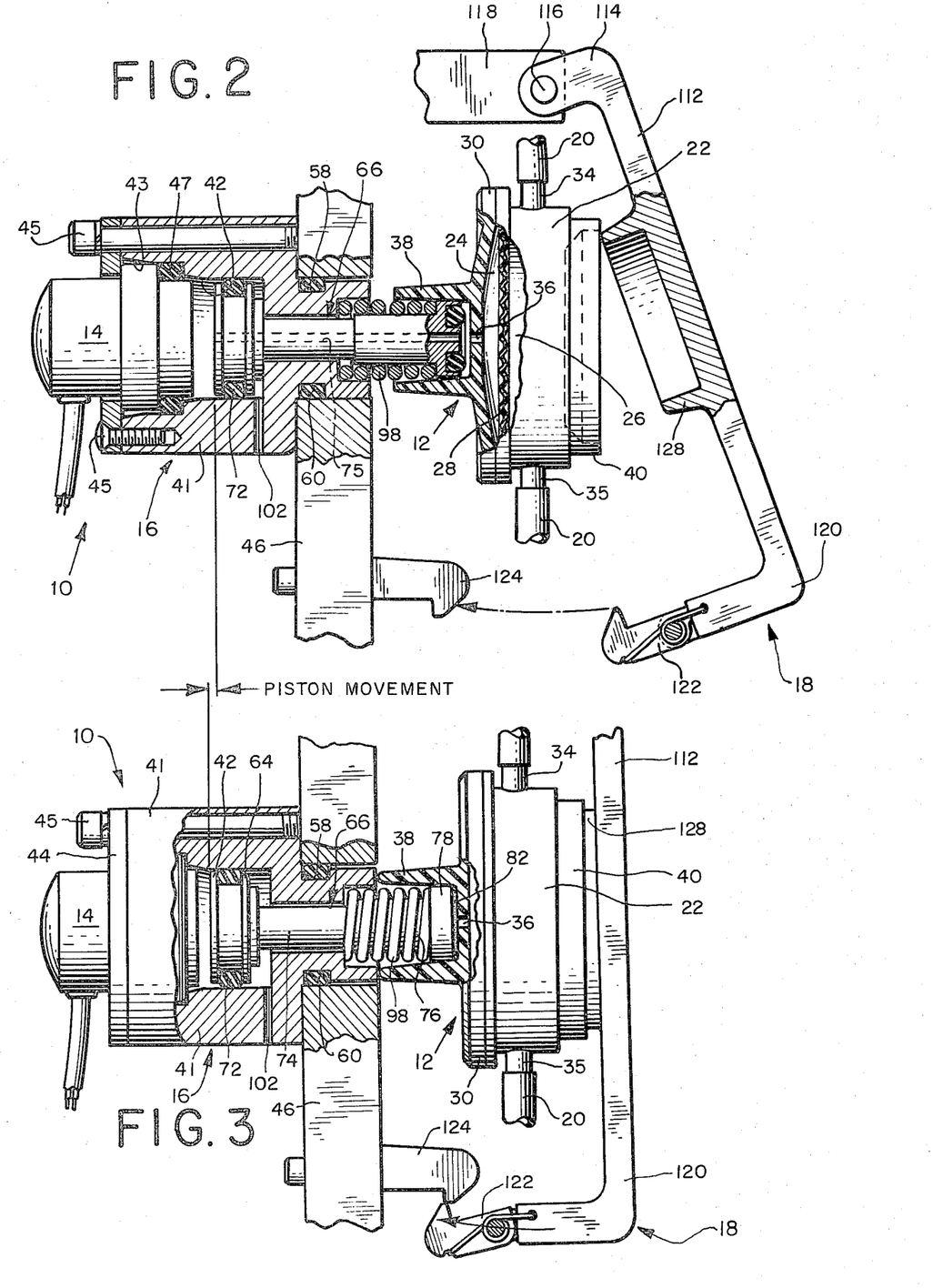
FIG. 2 is a part sectional view of the pressure monitoring assembly before a pressure transfer device thereof is coupled to a pressure coupling mechanism thereof and is taken along line 2—2 of FIG. 5.
FIG. 3 is a part sectional view of the pressure monitoring assembly similar to FIG. 2 and shows the position of a piston of the pressure coupling mechanism in the operational position and the displacement thereof from the position of the piston shown in FIG. 2.
Figure 5:
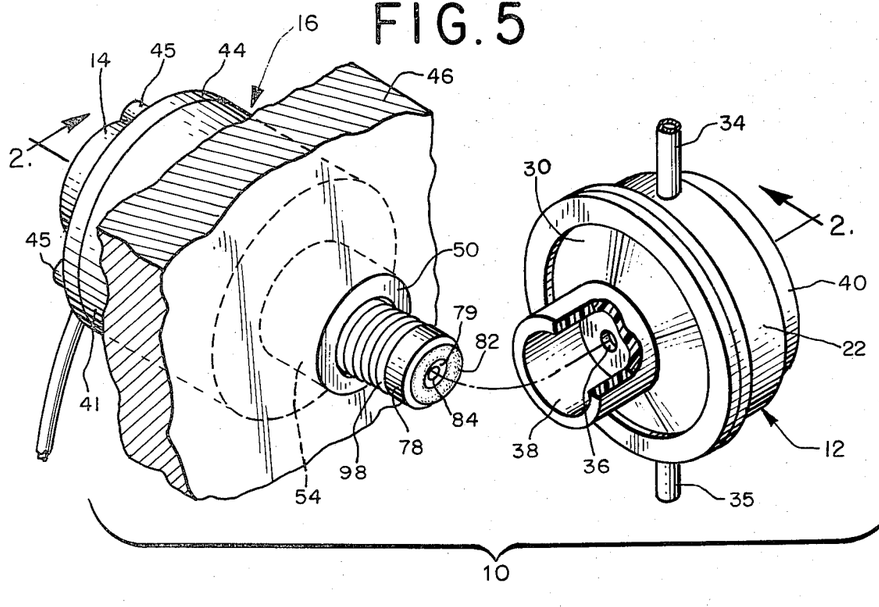
FIG. 5 is a perspective view of the pressure monitoring assembly with the pressure transfer device pivotally separated from the pressure coupling mechanism.

As best shown in FIGS. 1, 2 and 3, the pressure transfer device 12 includes a short cylindrical, saucer shaped capsule 22 having a hollow interior which is divided into first and second chambers 24 and 26 by a flexible diaphragm 28. The capsule has first and second sidewalls 30 and 32 and inlet and outlet ports 34 and 35 located in the periphery of the capsule 22. The ports 34 and 35 communicate with the second chamber 26 which is defined between the diaphragm 28 and the second sidewall 32.

The pressure transfer device 12 is a commercially available device designed to transfer liquid pressure in the second chamber 26 to the first chamber 24 containing air so that the liquid need not come in contact with the transducer 14 which measures the pressure. Also, the pressure transfer device 12 is disposable so that liquids such as blood need not be contaminated by previous samples passing through the pressure transfer device 12 and so that non-invasive monitoring of the liquid pressure can be obtained.

The flexible diaphragm 28 moves back and forth as the liquid pressure in the second chamber 26 changes and such pressure changes are transmitted to the first chamber 24. In a previous assembly the transducer 14 was coupled directly to the outer surface of first sidewall 30 of the first chamber 24 which has an orifice 36 therethrough for communicating the first chamber 24 with the transducer 14. As will be described in greater detail hereinafter, the assembly 10 of the present invention utilizes the pressure coupling mechanism 16 for coupling the pressure transfer device 12 to the pressure transducer 14 in such a way that a predetermined biasing pressure is established in the first chamber 24.

The pressure transfer device 12 also has a cylindrical sleeve 38 which protrudes from the first sidewall 30 coaxial to the orifice 36 for coupling and aligning a pressure transducer, or as in the present assembly 10, the pressure coupling mechanism 16 to the pressure transfer device 12. The pressure transfer device 12 further includes a locating rim 40 for aligning the pressure transfer device 12 with the latching mechanism 18, described in greater detail below. The rim 40 protrudes from the second sidewall 32 and is coaxial with the cylindrical sleeve 38 on the first sidewall 30.

In previous assemblies, the pressure changes in the pressure transfer device 12 were transmitted directly to the transducer 14 through an air passageway including the first chamber 24 containing air at atmospheric pressure. It was found that such assembly led to inaccurate pressure measurements when the pressure of the liquid being measured was significantly above or below atmospheric pressure. This was the result of pressure losses across the diaphragm 28 caused by stretching of the diaphragm 28.

Figure 6:
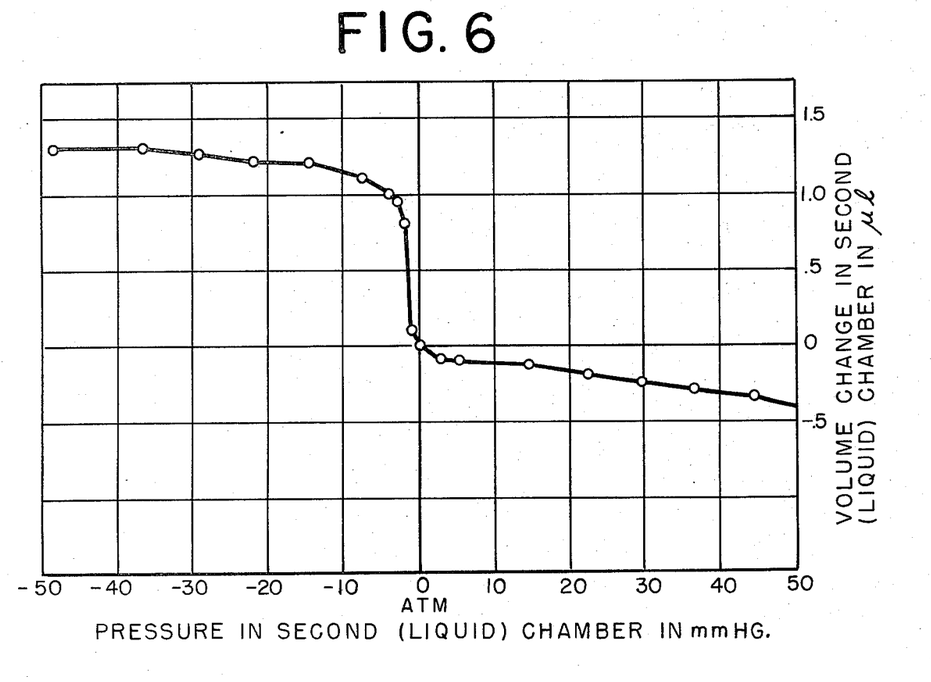
FIG. 6 is a graph of volume change in a liquid chamber in the pressure transfer device relative to the pressure change in the liquid chamber as the pressure is changed from a negative pressure to a positive pressure to show the maximum volume change and minimum loss across a diaphragm separating the liquid chambers from an air chamber when the pressure in the liquid chamber is close to atmospheric pressure.

Studies were conducted to examine the movement of the diaphragm 28 with pressure change of the liquid. In FIG. 6 is a graph reflecting on the abscissa the liquid pressure in the second chamber 26 in mm. Hg. above or below atmosphere and on the ordinate the volume change in the second chamber 26 in ul for a change in pressure in the second chamber 26. It is to be noted that when the liquid pressure is at about atmospheric pressure, that is, nearly equal to the pressure in the first chamber 24, a slight change in pressure is reflected in a large change in volume. It can be seen from the graph that as the liquid pressure changes from 5 mm. to −15 mm. there is a change in volume of 1.3 ul. On the other hand, pressure changes from −15 to −35 mm. or from 5 to 25 mm. cause volume changes of only about 0.1 ul. The large change in volume when there is nearly equal pressure on both sides of the diaphragm 28 is due to the freedom of movement of the flaccid, flexible diaphragm 28. When there is a significant pressure difference between the pressures in the two chambers 24 and 26, the diaphragm 28 is tautly bulged to one side or the other. The diaphragm 28 has little freedom of movement and additional pressure from the higher pressured side of the diaphragm will result in stretching of the diaphragm 28. Thus, volume changes at unequal pressures are the result of stretching or contracting of the diaphragm 28. This stretching and contracting requires work to be done by the liquid passing through the second chamber 26. When the liquid pressure in the second chamber 26 must work to stretch the diaphragm 28, pressure losses are incurred as the liquid acts on the diaphragm thus causing inaccurate pressure measurements. Because moving the flaccid diaphragm 28 requires less work than stretching a taut diaphragm, less pressure is lost when the pressures on both sides of the diaphragm 28 are nearly equal.

With a view toward minimizing the pressures losses across the diaphragm 28 due to stretching of the diaphragm 28, a positive biasing pressure can be established in the first chamber 24 of the pressure transfer device 12 equal to the expected normal pressure of the liquid whose pressure is to be monitored. According to the teachings of the present invention, the positive biasing pressure is developed by trapping a volume of air and compressing the trapped air in the pressure coupling mechanism 16. The biasing pressure developed is determined by the volume change of the trapped air according to the well known formula $PV=nRT$. Such biasing pressure also positions the diaphragm 28 initially toward the second sidewall 32 so that when the liquid is introduced into the second chamber 26 equalizing the pressure, the diaphragm 28 is positioned approximately in the center of the capsule 22.

As shown in FIGS. 1, 2 and 3, the pressure coupling mechanism 16 includes a cylindrically shaped body 41. The body 41 has a cylindrical chamber 42 therein. At one end of the body 41 is an opening 43 which is coextensive with the cylindrical chamber 42 and which is sized to receive the transducer 14 forming a first end of the cylindrical chamber 42. An end plate 44 holds the transducer 14 in the body and is fastened to the body by two screws 45, one of which also serves to hold the body 41 to a first frame member 46 of the centrifugal liquid processing apparatus. An O ring 47 around the transducer 14 air tightly seals the transducer 14 to the body 41.

The body 41 also has a passageway 48 therethrough between a second end 49 of the cylindrical chamber 42 and a coupling end 50 of the body 41. The coupling end 50 is countersunk providing an annular space 52 around the passageway 48.

The body 41 includes a narrowed-in-diameter portion 54 at the coupling end 50 which extends through the first frame member 46 of the centrifugal liquid processing apparatus. Around this narrowed-in-diameter portion 54 is an annular groove 58 which seats an O ring 60 for cushioning the pressure coupling mechanism 16 in the first frame member 46.

As best shown in FIG. 4, the pressure coupling mechanism 16 includes a piston assembly 62 including a piston 64 and a piston shaft 66 extending through the passageway 48 and beyond the coupling end 50. The piston assembly 62 has a through-bore 68 for communicating the first chamber 24 of the pressure transfer device with the cylindrical chamber 42.

As shown in FIGS. 1, 2 and 3, piston 64 has an annular groove 70 around its outer cylindrical periphery and an O ring 72 seated therein to establish an air tight seal between the piston 64 and the sidewall 30 of the cylindrical chamber 42 around the orifice 36.

The piston shaft 66 is constructed in two sections. The first section 74 is integral with the piston 64 and has a first portion 75 of the through-bore therein. The second section 76 extends from the body 41 and couples with the pressure transfer device 12. The second section 76 of the piston shaft 66 includes an annular flange 78 at an outer end 79 of the second section. On the face of the outer end 79 is an annular groove 80 which encircles the through-bore 68 and which seats an O ring 82 to seal with the pressure transfer device 12 when the pressure transfer device 12 is coupled to the pressure coupling mechanism 16.

The interior of the second section 76 of the piston shaft 66 has a second portion 84 of the through-bore 68 therein extending from the outer end 79 and opening into a larger threaded bore 86 which screws onto a reduced-in-diameter threaded protrusion 88 extending from the end of the first section 74 of the shaft 66. Opening from the threaded bore 86 is a wider extension 90 to receive the first section 74 of the shaft 66 and seal with an O ring 92 positioned in an annular groove 94 around the first section 74 of the shaft 66 so that the first portion 75 of the through-bore 68 in the first section 74 of the shaft 66 is in fluid tight communication with the second portion 84 of the through-bore 68.

A spring 98 is received in the countersunk space 52 around the shaft 66 and bears against the flange 78 on the outer end 79 of the shaft 66 and biases the shaft 66 outward from the body 41 with piston 64 bearing against the second end 49 of the cylindrical chamber 42.

Also the body 41 has a vent 102 extending from the space between the second end 49 of the cylindrical chamber 42 and the piston 64 to the ambient atmosphere.

In order to hold the pressure transfer device 12 to the pressure coupling means 16 with the piston 64 compressed, the assembly 10 includes the latching mechanism 18 which is operable to latch the pressure transfer device 12 to the pressure coupling mechanism 16. The latching mechanism 18 includes an arm 112 which is pivotally mounted at a first end 114 thereof by means of a hinge 116 to a second frame member 118 of the centrifugal liquid processing apparatus. The second frame member 118 is fixed relative to the first frame member 46. At a second end 120 of the arm 112 a spring biased latch 122 is provided which is operable to latch to a keeper 124 fastened to the first frame member 46 by a fastener 126. Also, the arm 112 includes a cup shaped protrusion 128 for coupling with the locating rim 40 on the second sidewall 32 of the pressure transfer device 12 to align and hold the pressure transfer device 12 in proper position with respect to and against the pressure coupling mechanism 16.

As best shown in FIGS. 2 and 3, in mounting the components of the assembly 10, the narrowed-in-diameter section 54 of the body 41 is inserted in the first frame member 46 and held there by one of the screws 45. The pressure transfer device 12 is then positioned so that the cylindrical sleeve 38 is in position to receive the coupling end of the shaft 66 in anticipation of sealing with the shaft 66 as the locating rim 40 of the pressure transfer device 12 is received in the cup shaped protrusion 128 and the latching arm 112 is pivoted toward the pressure coupling mechanism 16.

In the non-engaged position shown in FIG. 2, the piston shaft 66 is pushed away from the transducer 14 by the spring 98 so that the piston 64 is held against the second end 49 of the cylindrical chamber 42. As the arm 112 is pivoted, the cup shaped protrusion on the arm 112 is coupled with the locating rim 40 of the pressure transfer device 12. The pressure transfer device 12 is then pushed toward the pressure coupling mechanism 16 and the O ring 82 at the end of the shaft 66 forms an air tight seal with the pressure transfer device 12. When the seal is formed, the first chamber 24, the through-bore 68 and the portion of the cylindrical chamber 42 between the piston 64 and the transducer 16 forms a sealed air passageway. As the arm 112 continues to be pivoted toward the pressure coupling mechanism 16, the piston assembly 62 is pushed toward the transducer 16 reducing the volume between the piston 64 and the transducer 14. In doing so, a biasing pressure is established.

This biasing pressure then urges the diaphragm 28 toward the second sidewall 32. The pivoting of the arm 112 is stopped when the cylindrical sleeve 38 contacts the body 41. When the sleeve 38 abuts the body 41, the latch 122 is in position to be releasably latched to the keeper 124. The assembly is then ready to receive liquid in the second chamber 26 of the pressure transfer device 12 and monitor the pressure of same.

In the use of the pressure monitoring assembly 10 in a centrifugal liquid processing apparatus of the type disclosed in application Ser. No. 843,223, it is necessary to monitor three different pressures. One pressure is referred to as the Hi-Lo pressure condition where the sensor provides an alarm signal for a low pressure of −50 mm. Hg. gauge pressure and an alarm signal for a high pressure of +200 mm. Hg. gauge pressure and where the expected normal pressure is +50 mm. Hg. gauge. For this pressure monitoring, the assembly 10 used therefor is constructed with a piston 64 and cylindrical chamber 42 diameter and lengths for shaft 66 and chamber 42 which will provide a biasing pressure of approximately +50 mm. Hg. gauge when the pressure transfer device 12 is latched to the pressure coupling mechanism 16.

Another pressure to be monitored is a blocked line pressure condition where the alarm for high pressure is for a pressure of up to +750 mm. Hg. gauge and the expected normal pressure is +200. Here again the component parts of the assembly 10 used to monitor this "blocked line" pressure condition are dimensioned so that a biasing pressure of +200 mm. Hg. gauge is established when the pressure transfer device 12 is latched to the pressure coupling mechanism 16.

A further pressure to be monitored is an "occluded vein" pressure condition where the sensor provides an alarm signal when the pressure is −125 mm. Hg. gauge and the expected normal pressure is −25 mm. Hg. gauge. For this pressure monitoring, a conventional transducer is coupled directly to a pressure transfer device without the use of the pressure coupling mechanism 16.

From the foregoing description it will be apparent that the pressure monitoring assembly 10 including the pressure coupling mechanism 16 of the present invention provide a number of advantages, some of which have been described above and others of which are inherent in the invention. Also, obvious modifications can be made to the pressure monitoring assembly 10 without departing from the teachings of the invention. Accordingly, the scope of the invention is only to be limited as necessitated by the accompanying claims.

I claim:

1. Pressure coupling means for coupling a first chamber in a fluid pressure transfer device to a pressure transducer, the chamber having one wall thereof defined by a flexible diaphragm against which fluid pressure to be monitored acts, for establishing a fluid tight air passageway communicating the first chamber in the pressure transfer device to the pressure transducer and for establishing, when coupled between the pressure transfer device and the pressure transducer, a biasing force in said air passageway and the first chamber whereby the diaphragm is urged toward the fluid to be monitored so that when such fluid is present at its expected normal pressure, the diaphragm is in a relaxed unstretched state, said pressure coupling means comprising means for trapping a volume of air in said air passageway and the first chamber when said pressure coupling means is coupled to the pressure transfer device and means for compressing the volume of air in said air passageway and the first chamber to establish a biasing pressure in said air passageway and the first chamber.

2. The pressure coupling means according to claim 1 comprising a body having a coupling end and a cylindrical chamber in said body, a piston positioned for movement within said cylindrical chamber between first and second ends thereof, means for mounting the transducer to said body in air tight communication with said first end of said cylindrical chamber, said body having a passageway therein communicating with said second end of said cylindrical chamber and opening onto said coupling end, a shaft received in said passageway and having a first inner end fixed to said piston and a second outer end extending out of said passageway beyond said coupling end of said body, said piston and shaft having a through-bore extending therethrough, said through-bore communicating at one end thereof with said cylindrical chamber and opening at the other end thereof onto said second end of said shaft for communication with the first chamber in the pressure transfer device, compressible biasing means for biasing said shaft outwardly from said body, said biasing means urging said shaft outwardly from said coupling end of said body with said piston bearing against said second end of said cylinder and being compressible upon engagement of said outer end of said shaft with said pressure transfer device when said pressure coupling means is pushed against said pressure transfer device.

3. The pressure coupling means according to claim 2 wherein said trapping means includes sealing means on said second outer end of said shaft for establishing air tight communication between the first chamber in the pressure transfer device and said other end of said through-bore when said pressure coupling means is pushed against said pressure transfer device first to seal the area of communication between the first chamber in the pressure transfer device and said other end of said through-bore and second to establish a biasing pressure in said air passageway defined by said through-bore and the volume in said cylindrical chamber between said piston and said first end of said cylindrical chamber as said piston is moved toward said first end of said cylindrical chamber thereby reducing said volume and compressing the air trapped therein.

4. The pressure coupling means according to claim 3 wherein said second outer end of said shaft has an annular groove on the end face thereof around said through-bore in said shaft, and wherein a flexible O ring is seated in said annular groove and forms said sealing means which form an air tight seal with the pressure transfer device around an orifice in a wall of the pressure transfer device communicating with the first chamber when the pressure transfer device is coupled to said pressure coupling means.

5. The pressure coupling means according to claim 1 comprising a body having a coupling end and a cylindrical chamber in said body, a piston positioned for movement within said cylindrical chamber between first and second ends thereof, means for mounting the transducer to said body in air tight communication with said first end of said cylindrical chamber, said body having a passageway communicating with said second end of said cylindrical chamber and opening onto said coupling end, a shaft received in said passageway and having a first inner end fixed to said piston and said second outer end extending out of said passageway beyond said coupling end of said body, said piston and shaft having a through-bore extending therethrough, said through-bore communicating at one end thereof onto said second end of said shaft for communication with the first chamber in the pressure transfer device, said trapping means including sealing means at said outer end of said shaft for establishing air tight communication between the first chamber in the pressure transfer device and said other end of said through-bore, and said compressing means including compressible biasing means for biasing said shaft outwardly from said body, said biasing means urging said shaft outwardly from said coupling end of said body with said piston bearing against said second end of said cylinder and being compressible upon engagement of said sealing means with said pressure transfer device when said pressure coupling means is pushed against said pressure transfer device first to seal the area of communication between the first chamber in the pressure transfer device and said other end of said through-bore and second to establish a biasing pressure in said air passageway defined by said through-bore and the volume in said cylindrical chamber between said piston and said first end of said cylindrical chamber as said piston is moved toward said first end of said cylindrical chamber thereby reducing said volume and compressing the air trapped therein.

6. The pressure coupling means according to claim 5 wherein said second outer end of said shaft has an annular groove on the end face thereof and around said through-bore; and wherein said sealing means includes a flexible O ring seated in said annular groove with said O ring forming an air tight seal with the pressure transfer device around an orifice in a wall of said pressure transfer device communicating with the first chamber when the pressure transfer device is coupled to said pressure coupling means.

7. The pressure coupling means according to claim 2 wherein said biasing means is a spring which is received around said shaft between said body and said second outer end of said shaft.

8. The pressure coupling means according to claim 7 wherein said second outer end of said shaft has a circular flange; wherein said passageway for said shaft in said body is countersunk at said coupling end thereof to provide an annular space around said shaft; and wherein one end of said spring is received in said annular space and the other end of said spring bears against said flange.

9. The pressure coupling means according to claim 8 wherein said shaft includes a first section fixed to said piston and extending from said piston through said passageway and a second section including said circular flange at one end thereof and receiving thereon said spring; means for securing the other end of said second section with said first section; and means for forming a seal between said first section and said second section around said through-bore so that a first portion of said through-bore in said first section is in air tight communication with a second portion of said through-bore in said second section.

10. The pressure coupling means according to claim 9 wherein said sealing means includes an annular groove around said first section and an O ring seated thereon and adapted to seal with said second section; and wherein said securing means include a reduced-in-diameter threaded protrusion extending from the end of said first section, said second section including said second portion of said through-bore at one end thereof, a threaded bore larger than and opening from said second portion of said through-bore for receiving said threaded protrusion of said first section, and a larger-in-diameter bore extending from said threaded bore to receive said first section and seal with said O ring positioned around said first section.

11. The pressure coupling means according to claim 2 wherein said piston has an annular groove around the outer cylindrical periphery thereof and an O ring is seated in said groove and establishes an air tight seal between said piston and the sidewall of said cylindrical chamber in said body.

12. The pressure coupling means according to claim 2 wherein said body has a vent port communicating the space in said cylindrical chamber between said piston and second end of said cylindrical chamber to ambient air to vent said space as said piston moves.

13. The pressure coupling means according to claim 2 wherein said body has an opening therein which is coextensive with said cylindrical chamber and which receives the transducer therein which closes off said cylindrical chamber to form said first end thereof.

14. The pressure coupling means according to claim 13 including an O ring around the transducer for forming an air tight seal between the transducer and said opening, an annular end plate received around and against the transducer for holding the transducer in said body and fasteners to attach said end plate to said body.

15. A pressure monitoring assembly comprising a fluid pressure transfer device having a first chamber therein which has one wall thereof defined by a flexible diaphragm against which fluid pressure to be monitored acts, a pressure transducer and pressure coupling means for coupling said first chamber to said pressure transducer, for establishing a fluid tight air passageway communicating said first chamber to said pressure transducer and for establishing, when coupled between said pressure transfer device and said pressure transducer, a biasing force in said air passageway and said first chamber whereby said diaphragm is urged toward the fluid to be monitored so that when such fluid is present at its expected normal pressure said diaphragm is in a relaxed unstretched state, said pressure coupling means comprising means for trapping a volume of air in said air passageway and said first chamber when said pressure coupling means is coupled to said pressure transfer device and means for compressing the volume of air in said air passageway and said first chamber to establish a biasing pressure in said air passageway and said first chamber.

16. A pressure monitoring assembly according to claim 15 wherein said pressure coupling means comprises a body having a coupling end and a cylindrical chamber in said body, a piston positioned for movement within said cylindrical chamber between first and second ends thereof, means for mounting said transducer to said body in air tight communication with said first end of said cylindrical chamber, said body having a passageway therein communicating with said second end of said cylindrical chamber and opening onto said coupling end, a shaft received in said passageway and having a first inner end fixed to said piston and a second outer end extending out of said passageway beyond said coupling end of said body, said piston and shaft having a through-bore extending therethrough, said through-bore communicating at one end thereof with said cylindrical chamber and opening at the other end thereof onto said second end of said shaft for communication with said first chamber in said pressure transfer device, compressible biasing means for biasing said shaft outwardly from said body, said biasing means urging said shaft outwardly from said coupling end of said body with said piston bearing against said second end of said cylinder and being compressible upon engagement of said outer end of said shaft with said pressure transfer device when said pressure coupling means is pushed against said pressure transfer device.

17. The pressure monitoring assembly according to claim 16 wherein said trapping means includes sealing means on said second outer end of said shaft for establishing air tight communication between said first chamber in said pressure transfer device and said other end of said through-bore when said pressure coupling means is pushed against said pressure transfer device first to seal the area of communication between the first chamber in said pressure transfer device and said other end of said through-bore and second to establish a biasing pressure in said air passageway defined by said through-bore and the volume in said cylindrical chamber between said piston and said first end of said cylindrical chamber as said piston is moved toward said first end of said cylindrical chamber thereby reducing said volume and compressing the air trapped therein.

18. The pressure monitoring assembly according to claim 17 wherein said second outer end of said shaft has an annular groove on the end face thereof around said through-bore in said shaft; and wherein a flexible O ring is seated in said annular groove and forms said sealing means which forms an air tight seal with said pressure transfer device around an orifice in a wall of the pressure transfer device communicating with said first chamber when said pressure transfer device is coupled to said pressure coupling means.

19. The pressure monitoring assembly according to claim 15 comprising a body having a coupling end and a cylindrical chamber in said body, a piston positioned for movement within said cylindrical chamber between first and second ends thereof, means for mounting said transducer to said body in air tight communication with said first end of said cylindrical chamber, said body having a passageway communicating with said second end of said cylindrical chamber and opening onto said coupling end, a shaft received in said passageway and having a first inner end fixed to said piston and said second outer end extending out of said passageway beyond said coupling end of said body, said piston and shaft having a through-bore extending therethrough, said through-bore communicating at one end thereof onto said second end of said shaft for communication with said first chamber in said pressure transfer device, said trapping means including sealing means at said outer end of said shaft for establishing air tight communication between said first chamber in said pressure transfer device and said other end of said through-bore, said compressing means including compressible biasing means for biasing said shaft outwardly from said body, said biasing means urging said shaft outwardly from said coupling end of said body with said piston bearing against said second end of said cylinder and being compressible upon engagement of said sealing means with said pressure transfer device when said pressure coupling means is pushed against said pressure transfer device first to seal the area of communication between said first chamber in said pressure transfer device and said other end of said through-bore and second to establish a biasing pressure in said air passageway defined by said through-bore and the volume in said cylindrical chamber between said piston and said first end of said cylindrical chamber as said piston is moved toward said first end of said cylindrical chamber thereby reducing said volume and compressing the air trapped therein.

20. The pressure monitoring assembly according to claim 19 wherein said second outer end of said shaft has an annular groove on the end face thereof and around said through-bore; and wherein said sealing means includes a flexible O ring seated in said annular groove with said O ring forming an air tight seal with said pressure transfer device around an orifice in a wall of said pressure transfer device communicating with said first chamber when said pressure transfer device is coupled to said pressure coupling means.

21. The pressure monitoring assembly according to claim 16 wherein said biasing means is a spring which is received around said shaft between said body and said second outer end of said shaft.

22. The pressure monitoring assembly according to claim 21 wherein said second outer end of said shaft has a circular flange; wherein said passageway for said shaft in said body is countersunk at said coupling end thereof to provide an annular space around said shaft; and wherein one end of said spring is received in said annular space and the other end of said spring bears against said flange.

23. The pressure monitoring assembly according to claim 22 wherein said shaft includes a first section fixed to said piston and extending from said piston through said passageway and a second section including said circular flange at one end thereof and receiving thereon said spring; means for securing the other end of said second section with said first section; and means for forming a seal between said first section and said second section around said through-bore so that a first portion of said through-bore in said first section is in air tight communication with a second portion of said through-bore in said second section.

24. The pressure monitoring assembly according to claim 23 wherein said sealing means includes an annular groove around said first section and an O ring seated thereon and adapted to seal with said second section; and wherein said securing means includes a reduced-in-diameter threaded protrusion extending from the end of said first section, said second section including said second portion of said through-bore for receiving said threaded protrusion of said first section, and a larger-in-diameter bore extending from said threaded bore to receive said first section and seal with said O ring positioned around said first section.

25. The pressure monitoring assembly according to claim 16 wherein said piston has an annular groove around the outer cylindrical periphery thereof and an O ring is seated in said groove and establishes an air tight seal between said piston and the sidewall of said cylindrical chamber in said body.

26. The pressure monitoring assembly according to claim 16 wherein said body has a vent port communicating the space in said cylindrical chamber between said piston and second end of said cylindrical chamber to ambient air to vent said space as said piston moves.

27. The pressure monitoring assembly according to claim 16 wherein said body has an opening therein which is coextensive with said cylindrical chamber and which receives said transducer therein which closes off said cylindrical chamber to form said first end thereof.

28. The pressure monitoring assembly according to claim 27 including an O ring around said transducer for forming an air tight seal between said transducer and said opening, an annular end plate received around and against said transducer for holding said transducer in said body and fasteners to attach said end plate to said body.

29. The pressure monitoring assembly according to claim 15 wherein said pressure transfer device comprises a capsule with a hollow interior and said flexible diaphragm extends across said hollow interior and divides same into said first chamber and a second chamber, said capsule having an inlet port and an outlet port coupled respectively to opposite sides of said second chamber, said ports being connectible to a tubing carrying a liquid whose pressure is to be monitored and said flexible diaphragm transmits changes in pressure in said second chamber to said first chamber, and said capsule has an orifice in a sidewall thereof for communicating said first chamber with said air passageway in said pressure coupling means.

30. The pressure monitoring assembly according to claim 20 wherein said pressure transfer device includes an annular sleeve which protrudes from said pressure transfer device, which is coaxial with said orifice and which receives said second end of said shaft thereby aligning said orifice with said through-bore in said shaft, said annular sleeve bearing against said body of said pressure coupling means when said pressure transfer device is coupled with said pressure coupling means.

31. The pressure monitoring assembly according to claim 15 wherein said pressure monitoring assembly includes latching means for latching said pressure transfer device to said pressure coupling means.

32. The pressure monitoring assembly according to claim 31 wherein said pressure coupling means is mounted to a first frame member of a machine which utilizes said pressure monitoring assembly and wherein said latching means includes an arm which is pivotably mounted at one end on a second frame member of the machine which is fixed relative to the first member, means on said arm for receiving and engaging said pressure transfer device and for aligning said pressure transfer device with said pressure coupling means mounted to the first frame member when said arm is pivoted to bring said pressure transfer device in contact with said pressure coupling means, a latch on the other end of said arm and a keeper on the first frame member in position to engage and releasably keep said latch.

* * * * *